US012650415B2

(12) United States Patent
Lunden et al.

(10) Patent No.: US 12,650,415 B2
(45) Date of Patent: Jun. 9, 2026

(54) SIGNATURE DETECTION IN ENVIRONMENTAL DATA

(71) Applicant: Aclima Inc., San Francisco, CA (US)

(72) Inventors: Melissa M. Lunden, Berkeley, CA (US); Caroline Parworth, Walnut Creek, CA (US); Paul A. Solomon, Henderson, NV (US); Rishabh Urvesh Shah, Everett, WA (US); Davida Herzl, San Francisco, CA (US)

(73) Assignee: Aclima Inc., San Leandro, CA (US)

( * ) Notice: Subject to any disclaimer, the term of this patent is extended or adjusted under 35 U.S.C. 154(b) by 569 days.

(21) Appl. No.: 18/108,000

(22) Filed: Feb. 9, 2023

(65) Prior Publication Data

US 2023/0288390 A1 Sep. 14, 2023

Related U.S. Application Data

(60) Provisional application No. 63/332,117, filed on Apr. 18, 2022, provisional application No. 63/308,897, filed on Feb. 10, 2022.

(51) Int. Cl.
G01N 33/00 (2006.01)

(52) U.S. Cl.
CPC ................................ G01N 33/0062 (2013.01)

(58) Field of Classification Search
CPC ........... G01N 33/0062; G01N 33/0004; G01N 33/0047; G01N 33/0075; G01N 33/0068; G01N 33/0009; G01N 33/0022; G01N 33/0036; G01N 33/241; G01N 33/004; G01N 33/0031; G01N 33/0027; G01N 2015/0046; G01N 2015/0288; G01N 2015/1486; G01N 2015/1493; G01N 21/3504; G01N 2001/021;
(Continued)

(56) References Cited

U.S. PATENT DOCUMENTS 9,781,575 B1 * 10/2017 Wan ......................... H04W 4/33
11,366,057 B2 * 6/2022 Scott .................. G01N 33/0075
(Continued)

FOREIGN PATENT DOCUMENTS

CA 2390060 C * 7/2007 ............. B01D 46/62
CN 105136631 12/2015

OTHER PUBLICATIONS

Wei Yi et al, A Survey of Wireless Sensor Network Based Air Pollution Monitoring Systems, Sensors, vol. 15, No. 12, Dec. 12, 2015, pp. 31392-31427. (Year: 2015).*

*Primary Examiner* — Jeffrey P Aiello
(74) *Attorney, Agent, or Firm* — Van Pelt, Yi & James LLP

(57) ABSTRACT

A method for monitoring air quality is described. The method includes measuring environmental components at multiple locations using multiple mobile sensor platforms to provide sensor data. The environmental components include particulate matter having a size range and ambient gases. The sensor data includes particulate matter data having the size range and ambient gas data captured at the plurality of locations. The method also includes determining a signature based on the particulate matter data including the size range, and at least one additional factor. The at least one additional factor includes the ambient gas data. The method also includes identifying a source based on the signature.

13 Claims, 7 Drawing Sheets

(58) Field of Classification Search
CPC ......... G01N 2001/2223; G01N 1/2252; G01N 2291/0215; G01N 15/02; G01N 2021/1793; G01N 1/26; G06F 17/18; G06F 18/217; H04W 4/38; Y02A 50/20; Y02T 10/40
USPC ............ 73/23.31, 28.01, 1.06, 114.69, 1.02, 73/114.01, 23.2; 702/81, 188, 24, 22, 27, 702/127, 23, 116, 3, 2, 30, 1, 104
See application file for complete search history.

(56) References Cited

U.S. PATENT DOCUMENTS

| | | | | |
|---|---|---|---|---|
| 11,499,954 | B2 * | 11/2022 | Chadha | .............. G01N 33/0065 |
| 2021/0033586 | A1 * | 2/2021 | Chadha | .............. G01N 33/0065 |
| 2021/0072080 | A1 * | 3/2021 | Scott | ................... G02B 17/023 |

* cited by examiner

200

| Mobile Sensor Platform(s) Traverse Route(s) Collecting Position and Sensor Data | 202 |

Mobile Sensor Platforms Provide Position and Sensor Data — 204

Repeat Collecting and Sending Data on Additional Pass(es) Using Mobile Sensor Platform(s) — 206

300

320

310

312

312

324

310

314

322

400

500

600

700

800

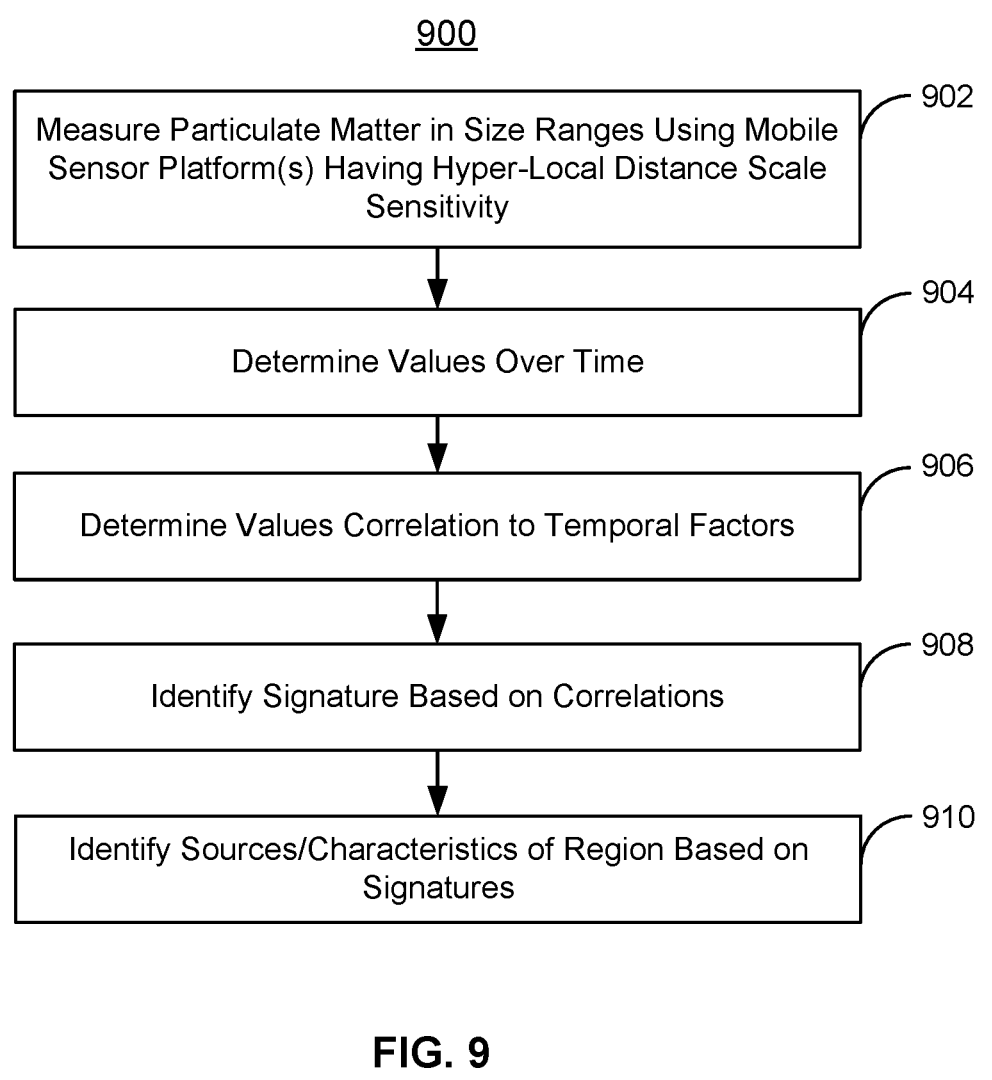

900

| |
|---|
| Measure Particulate Matter in Size Ranges Using Mobile Sensor Platform(s) Having Hyper-Local Distance Scale Sensitivity | 902 |

↓

| Determine Values Over Time | 904 |

↓

| Determine Values Correlation to Temporal Factors | 906 |

↓

| Identify Signature Based on Correlations | 908 |

↓

| Identify Sources/Characteristics of Region Based on Signatures | 910 |

FIG. 9

SIGNATURE DETECTION IN ENVIRONMENTAL DATA

CROSS REFERENCE TO OTHER APPLICATIONS

This application claims priority to U.S. Provisional Patent Application No. 63/308,897 entitled SIGNATURE DETECTION IN ENVIRONMENTAL DATA filed Feb. 10, 2022, and U.S. Provisional Patent Application No. 63/332,117 entitled DIESEL AND NON-DIESEL COMBUSTION AND OTHER SIGNATURE DETECTION IN ENVIRONMENTAL DATA filed Apr. 18, 2022, both of which are incorporated herein by reference for all purposes.

BACKGROUND OF THE INVENTION

Environmental monitoring measures the levels of various components in the surroundings (e.g. the air). The environmental data collected could facilitate the detection of potentially harmful air pollution, radiation, greenhouse gases, emissions from combustion or other or processes, or other contaminants in the environment. In order to assess the effects of such pollutants, however, it is desirable to identify the types of emissions and associate environmental data with specific sources. Although such an analysis would allow individuals, their communities, and regulators to evaluate the quality of their surroundings and mitigate risks, barriers exist to collecting and utilizing the environmental data to do so. Consequently, an improved mechanism for detecting sources of various environmental components is desired.

BRIEF DESCRIPTION OF THE DRAWINGS

Various embodiments of the invention are disclosed in the following detailed description and the accompanying drawings.

FIG. 9 is a flow chart depicting an embodiment of a method for monitoring environmental quality using signatures utilizing environmental data captured using mobile sensor platforms.

DETAILED DESCRIPTION

Figure 1:
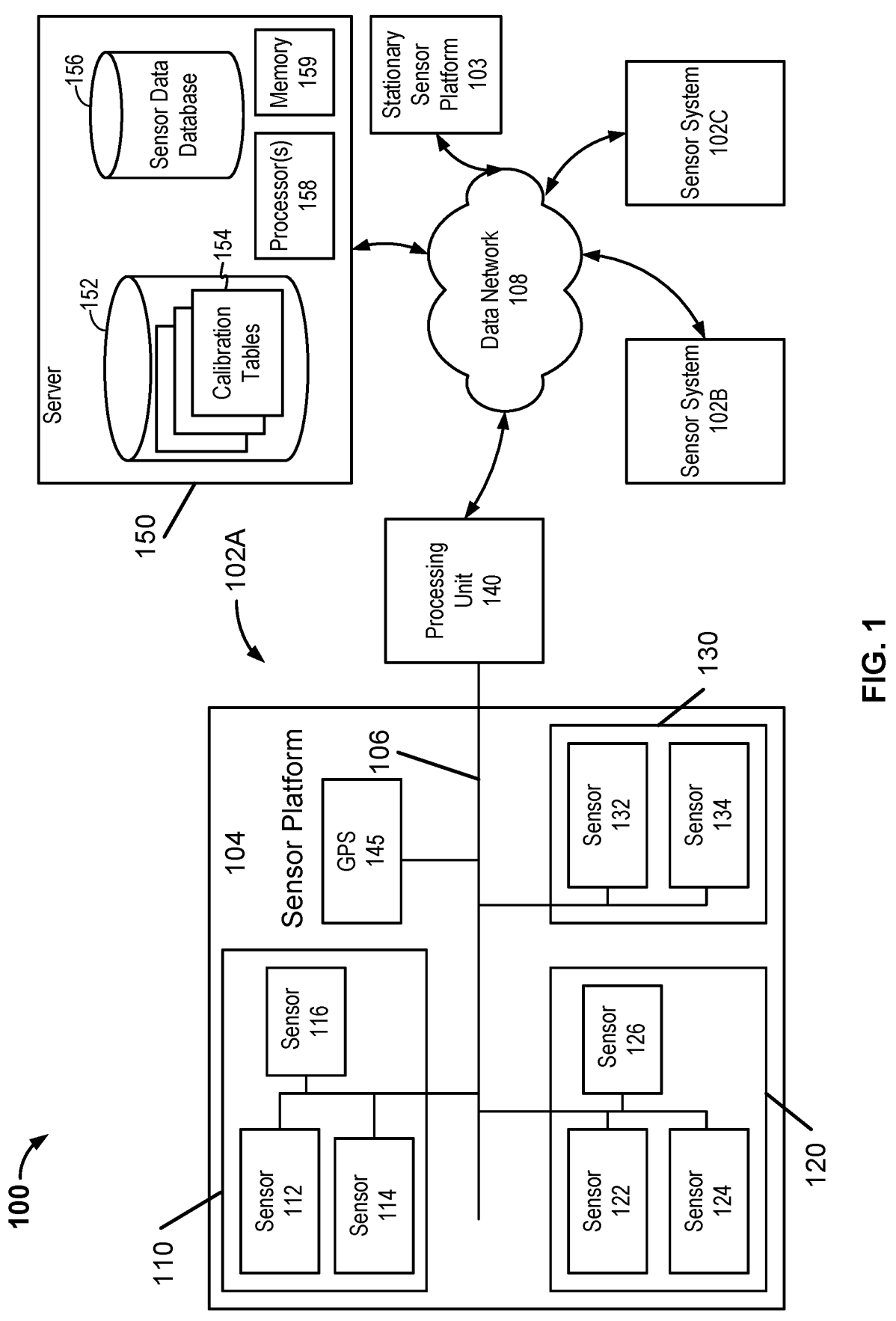
FIG. 1 depicts an embodiment of a system for capturing environmental data using mobile sensor platforms and associating the environmental data with map features.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A method for monitoring air quality is described. The method includes measuring environmental components at locations using a multiple mobile sensor platforms to provide sensor data. The environmental components include particulate matter having a size range and a plurality of ambient gases. The sensor data includes particulate matter data having the size range, speciated black and organic carbon particulate matter data, and ambient gas data captured at the locations. The method also includes determining a signature based on the particulate matter data and at least one additional factor. The at least one additional factor includes the ambient gas data. The method also includes identifying a source based on the signature. Determining the signature may further include determining, based on the particulate matter data and ambient gas data, means, medians, or other relevant statistical aggregation for the locations. Identifying the sources may include correlating the portion of the locations exhibiting enhancements in the statistical aggregation of the particulate matter data with the relevant statistical aggregation of the ambient gas data. These enhancements may be in absolute values of data, ratio(s) between different data (e.g. carbon monoxide data to carbon dioxide data), ratio(s) for the same type of data (e.g. particulate matter data captured at a location to an average, median, and/or other measure of the background), or other measures. An analogous computer program product and system including a processor and a memory are also described. In such a system, the memory may provide instructions to the processor and the processor may be configured to perform functions analogous to the method.

In some embodiments, the signature is a diesel combustion signature. In such embodiments, the ambient gas data includes nitrogen dioxide data. The particulate matter data includes black carbon data. The sensor data may also include (e.g. NO, $NO_x$ [$NO+NO_2$], CO, $CO_2$, CH4, C2H4, tVOC (total volatile organic compounds), VOC (volatile organic compounds), and/or other constituents of the environment measured using the mobile sensor platforms. Determining the signature includes determining the diesel combustion signature based on the nitrogen dioxide data indicating an ambient gas enhancement in nitrogen dioxide, and the black carbon data indicating an enhancement in black carbon. As used herein, black carbon is considered to be particulate matter, though may be measured using different technique(s) than, for example, particulate matter in the size range of 0.5 micrometers through fifteen micrometers. Further, nothing requires the chemical composition of different types and/or sizes of particulate matter to be the same. In some embodiments, an additional enhancement corresponding to a portion of the size range less than 0.5 micrometer (e.g. 0.3 micrometer to 0.5 micrometer) may also be considered for the diesel combustion signature. Other ambient gases may also be considered. For example, an enhancement in a ratio of nitrogen dioxide to carbon dioxide, a ratio of black carbon to carbon dioxide to black carbon and/or a ratio of particulate matter in the size range of less than 0.5 micrometers to carbon dioxide may also be used in determining the diesel combustion signature. In some embodiments, the enhancement may be considered to be a peak in statistical aggregation (e.g. mean or median) values, a peak in ratio(s) between statistical aggregations, or other measure of a level above noise or other background (e.g. twice, three multiplied by the background level, five multiplied by the background, ten multiplied by the background, or more) for the particulate matter and/or ambient gas data. For example, black carbon data measured that is two or three multiplied by a black carbon background may be considered an enhancement in black carbon. Background levels may include sensor baselines or noise, the average or median values for a region, readings taken after a rain or other event. Similarly, a peak in the amounts or volumes of particulate matter having a size less than 0.5 micrometers may be used as an enhancement. In another example, a peak in the ratio of particulate matter having a size less than 0.5 micrometers to particulate matter having a size range of 1.0 micrometers to 2.5 micrometers may be used as the enhancement for determining the diesel combustion signature. In some embodiments, other portion (s) of the size range may be used to determine diesel (and/or other types of) combustion. For example, the size range may include particulate matter having a size not exceeding 2.5 micrometers. In some embodiments, other (larger or smaller) sizes may be used (e.g. PM10, PM20, PM0.5). The diesel combustion source(s) may then be identified based on the diesel combustion signature. In some embodiments, the source is an area of spatial impact and the diesel combustion signature indicates the area of spatial impact has higher or lower diesel emissions than another region.

In some embodiments, the additional factor(s) further include at least one of a temporal factor indicating a wildfire or a geographic factor indicating a railyard and shipping ports. In such embodiments determining the diesel combustion signature is determined for the temporal factor indicating an absence of a wildfire. Similarly, if the temporal factor indicates the presence of a wildfire, then a wildfire signature may be determined. Identifying the source further includes identifying the at least one diesel combustion source as a railyard and shipping ports based on the geographic factor indicating an airport.

In some embodiments, the signature is a non-diesel combustion signature and the ambient gases include carbon monoxide and carbon dioxide. In some embodiments, VOCs are also included. The ambient gas data includes carbon monoxide data, carbon dioxide data and, in some embodiments, VOC data. In such embodiments, the diesel combustion signature is determined based on the carbon dioxide data and the carbon monoxide data indicating an enhancement in a ratio of the carbon monoxide to the carbon dioxide, the VOC data indicating a VOC enhancement, and a lack of a particulate matter enhancement corresponding to black carbon. In some embodiments, an additional combustion signature (e.g., a restaurant signature) is determined based on an absence of an enhancement in the carbon monoxide data and the lack of the particulate matter enhancement for the black carbon.

In some embodiments, the additional factor(s) include at least one of a geographic area, mobile platform speed, or meteorological data. In such embodiments, determining the signature further includes determining a sea salt signature based on a portion of the particulate matter data having a size greater than 1.5 micrometers and a correlation between the geographic area and the locations or a correlation between the meteorological data and the locations. Further, a brake dust signature may be determined based on the portion of the particulate matter data having a size range greater than 1.5 micrometers and correlation with mobile platform speed. The source may be identified as a sea spray source based on the sea salt signature or a brake dust source based on the brake dust signature. Other signatures may be determined based on the ambient gas data, particulate matter data and/or other data captured by the mobile sensor platforms.

FIG. 1 depicts an embodiment of a system 100 for collecting and processing environmental data. System 100 includes multiple mobile sensor platforms 102A, 102B, 102C and server 150. In some embodiments, system 100 may also include one or more stationary sensor platforms 103, of which one is shown. Stationary sensor platform 103 may be used to collect environmental data at a fixed location. The environmental data collected by stationary sensor platform 103 may supplement the data collected by mobile sensor platforms 102A, 102B and 102C. Thus, stationary sensor platform 103 may have sensors that are the same as or analogous to the sensors for mobile sensor platforms 102A, 102B and 102C. In other embodiments, stationary sensor platform 103 may be omitted. Although a single server 150 is shown, multiple servers may be used. The multiple servers may be in different locations. Although three mobile sensor platforms 102A, 102B and 102C are shown, another number are typically present. Mobile sensor platforms 102A, 102B and 102C and stationary sensor platform(s) 103 may communicate with server 150 via a data network 108. The communication may take place wirelessly.

Mobile sensor platforms 102A, 102B and 102C may be mounted in a vehicle, such as an automobile or a drone. In some embodiments, mobile sensor platforms 102A, 102B and 102C are desired to stay in proximity to the ground to be better able to sense conditions analogous to what a human would experience. Mobile sensor platform 102A includes a bus 106, sensors 110, 120 and 130. Although three sensors are shown, another number may be present on mobile sensor platform 102A. In addition, a different configuration of components may be used with sensors 110, 120 and 130. Each sensor 110, 120 and 130 is used to sense environmental quality and may be of primary interest to a user of system 100. For example, sensors 110, 120 and 130 may be gas sensors, volatile organic compound (VOC) sensors, particulate matter sensors, radiation sensors, noise sensors, light sensors, temperature sensors, or other analogous sensors that capture variations in the environment. For example, sensors 110, 120 and 130 may be used to sense one or more of $NO_2$, CO, NO, $O_3$, $SO_2$, $CO_2$, VOCs, $CH_4$, $C_2H_6$, particulate matter, black carbon, organic carbon, noise, light, temperature, radiation, tVOCs, VOCs, other environmental components (e.g. other ambient gas(es)), and/or other parameters. In some embodiments, sensor 110, 120 and/or 130 may be a multi-modality sensor. A multi-modality gas sensor senses multiple gases or compounds. For example, if sensor 110 is a multi-modality $NO_2/O_3$ sensor, sensor 110 might sense both $NO_2$ and $O_3$ together.

Although not shown in FIG. 1, other sensors co-located with sensors 110, 120 and 130 may be used to sense characteristics of the surrounding environment including, in some instances, other gases and/or particulate matter. Such additional sensors are exposed to the same environment as sensors 110, 120 and 130. In some embodiments, such additional sensors are in close proximity to sensors 110, 120 and 130, for example within ten millimeters or less. In some embodiments, the additional sensors may be further from sensors 110, 120 and 130 if the additional sensors sample the same packet of air inside of a closed system, such as a system of closed tubes. In some embodiments, temperature and/or pressure are sensed by these additional sensors. For example, an additional sensor co-located with sensor 110 may be a temperature, pressure and relative humidity (T/P/RH) sensor. These additional co-located sensors may be used to calibrate sensors 110, 120 and/or 130. Although not shown, sensor platform 102A may also include a manifold for drawing in air and transporting air to sensors 110, 120 and 130 for testing.

Sensors 110, 120 and 130 provide sensor data over bus 106, or via another mechanism. In some embodiments, data from sensors 110, 120 and 130 incorporates time. This time may be provided by a master clock (not shown) and may take the form of a timestamp. Master clock may reside on sensor platform 102A, may be part of processing unit 140, or may be provided from server 150. As a result, sensors 110, 120 and 130 may provide timestamped sensor data to server 150. In other embodiments, the time associated with the sensor data may be provided in another manner. Because sensors 110, 120 and 130 generally capture data at a particular frequency, sensor data is discussed as being associated with a particular time interval (e.g. the period associated with the frequency), though the sensor data may be timestamped with a particular value. For example, sensors 110, 120 and/or 130 may capture sensor data every second, every two seconds, every ten seconds, or every thirty seconds. The time interval may be one second, two seconds, ten seconds or thirty seconds. The time interval may be the same for all sensors 110, 120 and 130 or may differ for different sensors 110, 120 and 130. In some embodiments, the time interval for a sensor data point is centered on the timestamp. For example, if the time interval is one second and a timestamp is t1, then the time interval may be from t1−0.5 seconds to t1+0.5 seconds. However, other mechanisms for defining the time interval may be used.

Sensor platform 102A also includes a position unit 145 that provides position data. In some embodiments, position unit 145 is a global positioning satellite (GPS) unit. Consequently, system 100 is described in the context of a GPS unit 145. The position data may be time-stamped in a manner analogous to sensor data. Because position data is to be associated with sensor data, the position data may also be considered associated with time intervals, as described above. However, in some embodiments, position data (e.g. GPS data) may be captured more or less frequently than sensor data. For example, GPS unit 145 may capture position data every second, while sensor 130 may capture data every thirty seconds. Thus, multiple data points for the position data may be associated with a single thirty second time interval. The position data may be processed as described below.

Optional processing unit 140 may perform some processing and functions for data from sensor platform 104, may simply pass data from sensor platform 104 to server 150 or may be omitted.

Mobile sensors platforms 102B and 102C are analogous to mobile sensor platform 102A. In some embodiments, mobile sensor platforms 102B and 102C have the same components as mobile sensor platform 102A. However, in other embodiments, the components may differ. However, mobile sensor platforms 102A, 102B and 102C function in an analogous manner.

Server 150 includes sensor data database 152, processor (s) 154, memory 156 and position data database 158. Processor(s) 154 may include multiple cores. Processor(s) 154 may include one or more central processing units (CPUs), one or more graphical processing units (GPUs) and/or one or more other processing units. Memory 156 can include a first primary storage, typically a random access memory (RAM), and a second primary storage area, typically a non-volatile storage such as solid state drive (SSD) or hard disk drive (HDD). Memory 156 stores programming instructions and data for processes operating on processor(s) 154. Primary storage typically includes basic operating instructions, program code, data and objects used by processor(s) 154 to perform their functions. Primary storage devices (e.g., memory 156) may include any suitable computer-readable storage media, described below, depending on whether, for example, data access needs to be bi-directional or unidirectional.

Sensor data database 152 includes data received from mobile sensor platforms 102A, 102B and/or 102C. After capture by mobile sensor platform 102A, 102B and/or 102C, sensor data stored in sensor data database 152 may be operated on by various analytics, as described below. Position data database 158 stores position data received from mobile sensor platforms 102A, 102B and/or 102C. In some embodiments, sensor data database 152 stores position data as well as sensor data. In such embodiments, position data database 158 may be omitted. Server 150 may include other databases and/or store and utilize other data. For example, server 150 may include calibration data (not shown) used in calibrating sensors 110, 120 and 130.

System 100 may be used to capture, analyze and provide information regarding hyper-local environmental data. Mobile sensor platforms 102A, 102B and 102C may be used to traverse routes and provide sensor and position data to server 150. Server 150 may process the sensor data and position data. Server 150 may also assign the sensor data to map features corresponding to the locations of mobile sensor platforms 102A, 102B and 102C within the same time interval as the sensor data was captured. As discussed above, these map features may be hyper-local (e.g. one hundred meter or less road segments or thirty meter or less road segments). Thus, mobile sensor platforms 102A, 102B and 102C may provide sensor data that can capture variations on this hyper-local distance scale. Server 150 may provide the environmental data, a score, confidence score and/or other assessment of the environmental data to a user. Thus, using system 100 hyper-local environmental data may be obtained using a relatively sparse network of mobile sensor platforms 102A, 102B and 102C, associated with hyper-local map features and processed for improved understanding of users.

Figure 2:
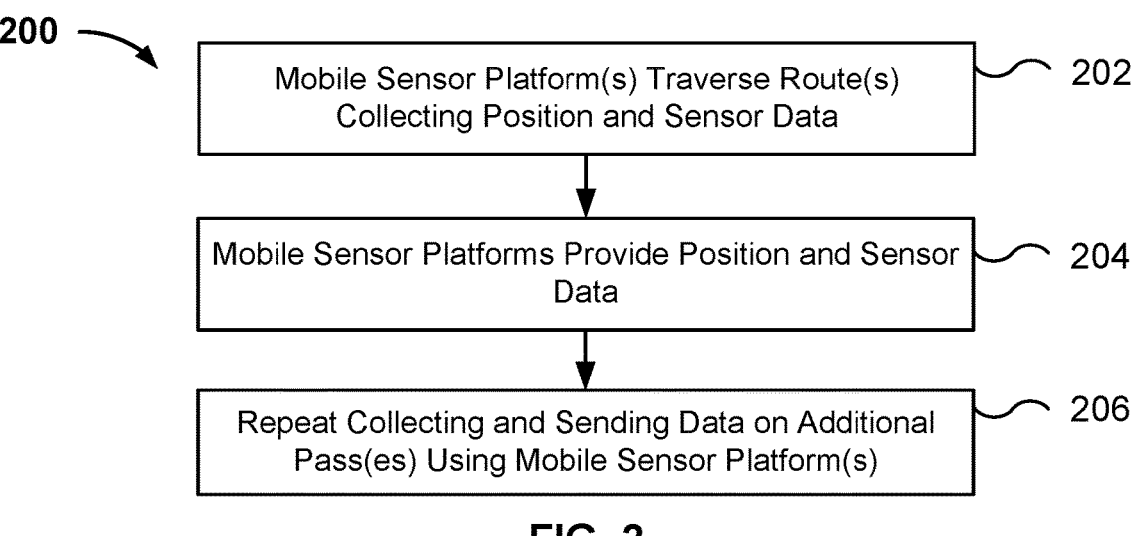
FIG. 2 depicts an embodiment of a method for capturing environmental data using mobile sensor platforms.

FIG. 2 depicts an exemplary embodiment of method 200 for capturing environmental data using mobile sensor platforms, such as mobile sensor platforms 102A, 102B and/or 102C. Method 200 is described in the context of system 100, but may be performed using other systems. For clarity, only some portions of method 200 are shown. Although shown in a sequence, in some embodiments, processes may occur in parallel and/or in a different order.

Mobile sensor platforms traverse routes in a geographic area, at 202. While traversing the routes, the mobile sensor platforms collect not only sensor data, but also position data. For example, a mobile sensor platform may sense one or more of $NO_2$, $CO$, $NO$, $O_3$, $SO_2$, $CO_2$, $CH_4$, $C_2H_6$, tVOCs, VOCs, particulate matter in one or more size ranges, black carbon, organic carbon, other compounds, radiation, noise, light and other environmental data at various times during traversal of the route. Other environmental characteristics, including but not limited to temperature, pressure, and/or humidity may also be sensed at 202. In addition, the time corresponding to the environmental data is also captured. The time may be in the form of a timestamp for the sensor data (sensor timestamp), which may correspond to a particular time interval. Different sensors on the mobile sensor platform may capture the environmental data at different times and/or at different frequencies. Also at 202 the mobile sensor platforms capture position data, for example via a GPS unit. The position data may include location (as indicated by a GPS unit), velocity and/or other information related to the geographic location of the mobile sensor platform. In some embodiments, position data from other sources, such as acceleration, may be captured from by the vehicle or another source. The position data may include a timestamp (position timestamp) or other indicator of the time at which the position data is captured.

The mobile sensor platforms provide the position and sensor data to a server, at 204. In some embodiments, mobile sensor platforms provide this data substantially in real time, as the mobile sensor platforms traverse their routes at 202. Thus, the position and sensor data may be transmitted wirelessly to the server. In some embodiments, some or all of the position and/or sensor data is stored at the mobile sensor platform and provided to the server at a later time. For example, the data may be transferred to the server when the mobile sensor platform returns to its base. In some embodiments, the mobile sensor platform may process the sensor data and/or position data prior to sending the sensor and/or position data to the server. In other embodiments, the mobile sensor platform provides little or no processing. The sensor data and position data may be sent at the same time or may be sent separately.

At 206, the route traversal and data collecting of 202 and data sending of 204 are repeated. Thus, the mobile sensor platforms may traverse the same or different routes at 206. In either case, multiple passes of the same geographic locations, and thus multiple passes of the same corresponding map features, are made at 206. In some embodiments, the repetition at 206 may be periodic (e.g. approximately every day, week, month, or other time period). In some embodiments, the repetition at 206 may be performed based on other timing. In some cases, the same mobile sensor platform is sent on the same route and/or collects data for the same map features. In some embodiments, different mobile sensor platforms collect data that may be used for the same routes and/or map features. Further, routes may be changed. Also at 206, steps 202 and 204 may be performed multiple times. Thus, at 206, data for a particular region may be aggregated over time.

Figure 3A:
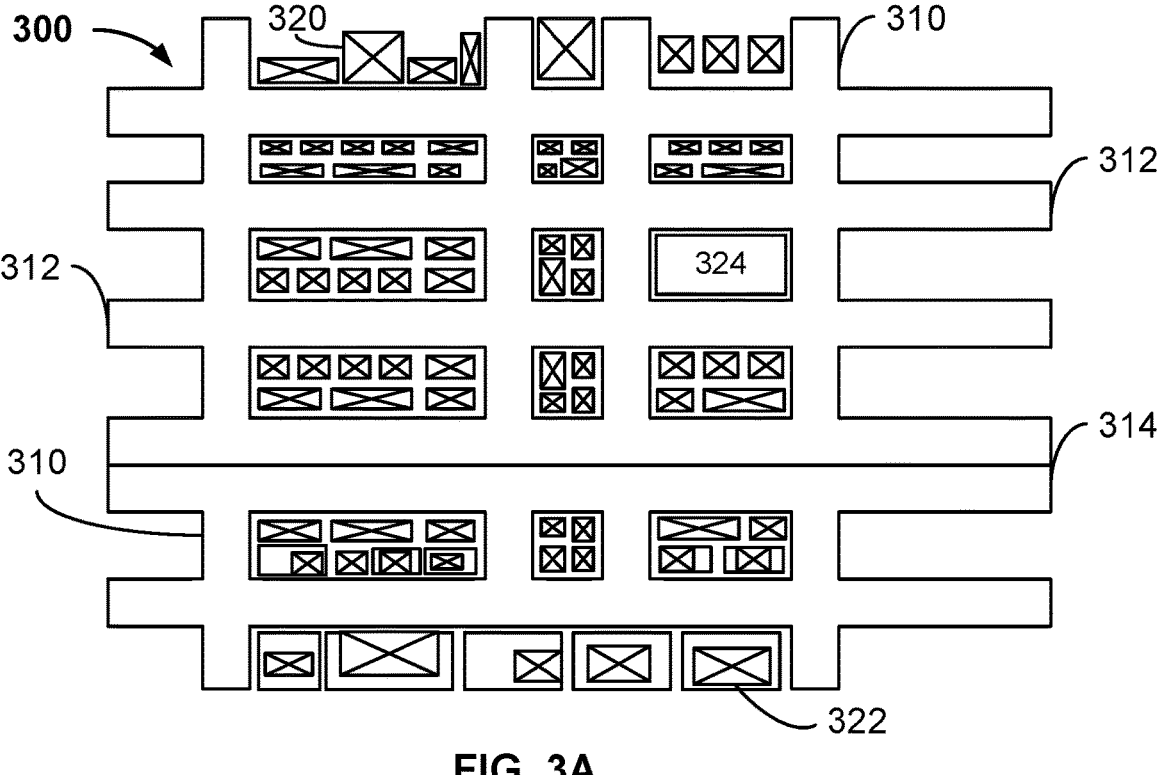
FIGS. 3A-3C illustrate a particular region and the embodiment of routes that may be traversed using a method for capturing environmental data using mobile sensor platforms.
Figure 3B:
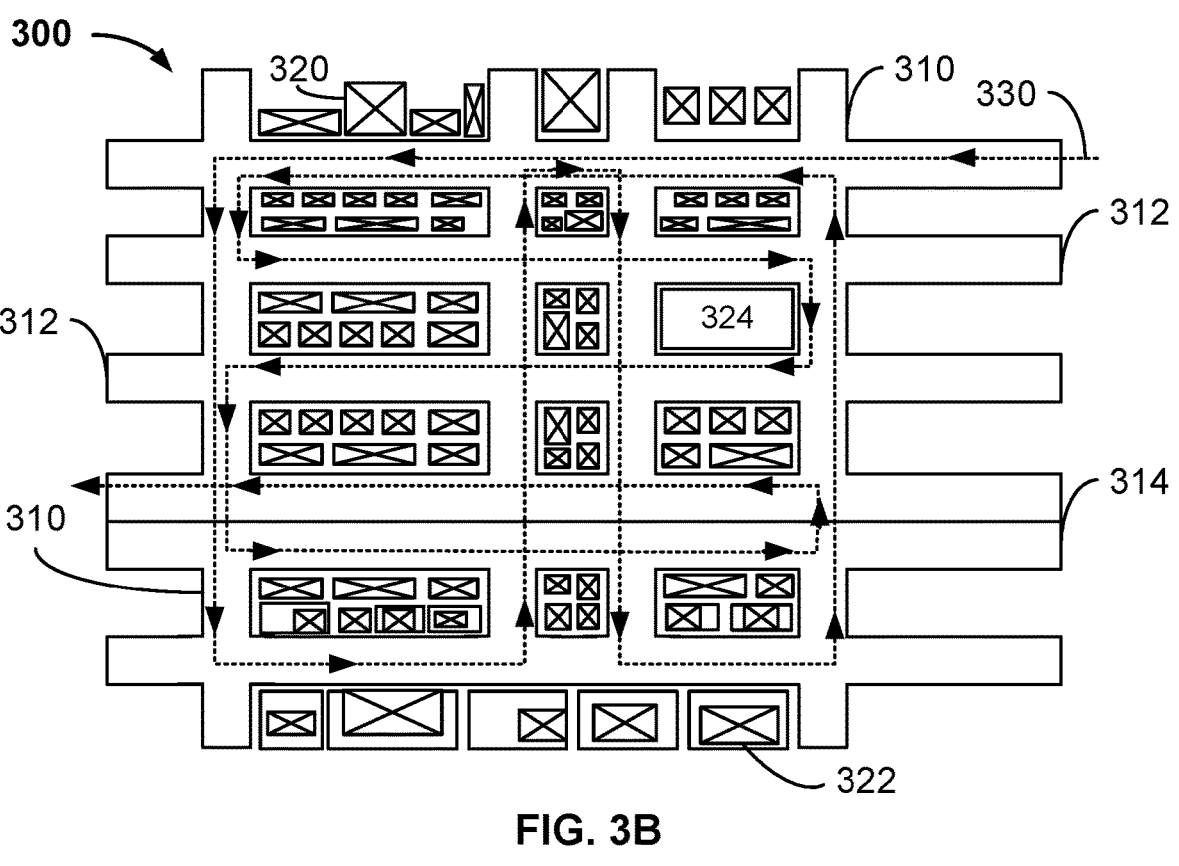
Figure 3C:
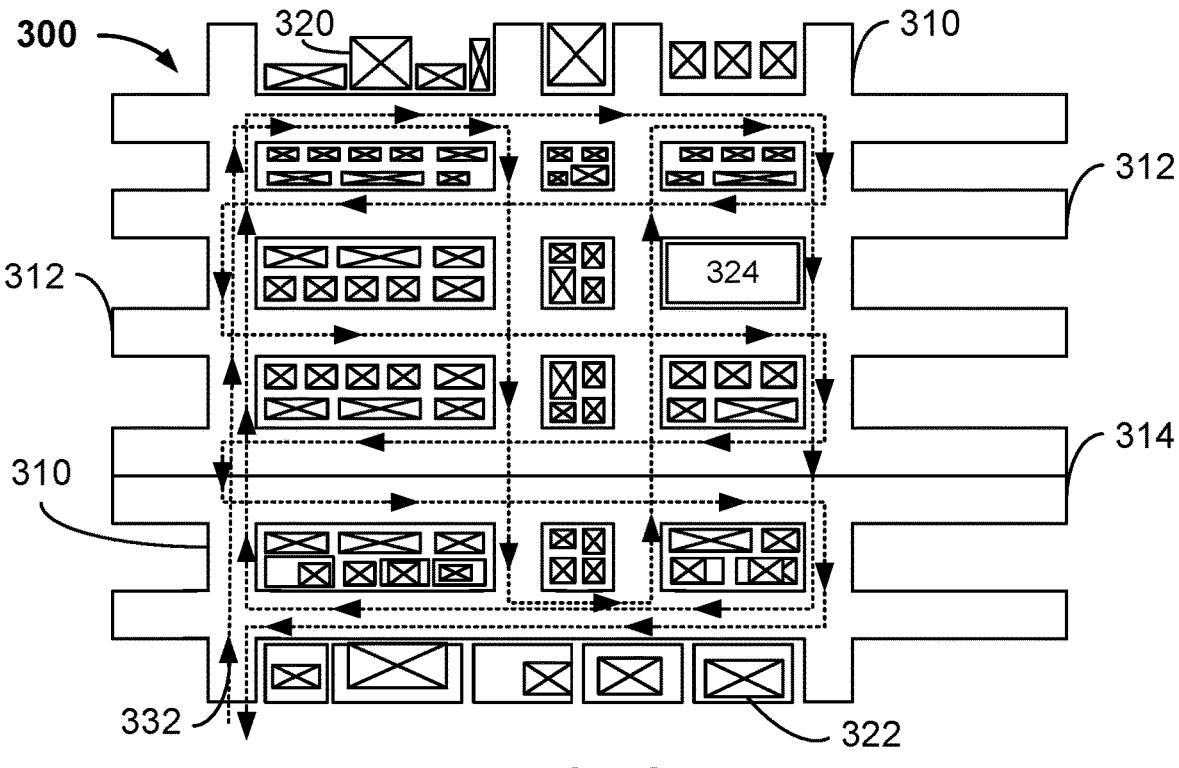

For example, FIGS. 3A-3C illustrate a particular geographic area and the routes that may be traversed using method 200. A map 300 corresponding to the geographic area is shown in FIG. 3A. Map 300 may be an open source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. Other mobile sensor platforms (e.g. mobile sensor platforms 102B and/or 102C) may traverse different routes at the same or overlapping times. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by GPS unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses different routes. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation and analysis. Sensor data and position data are sensed sufficiently frequently using method 200 that variations in environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

The sensor data captured and provided to server 150 is further processed. For example, data from multiple runs of mobile sensor platforms, such as mobile sensor platform 104, and stationary sensor data may be aggregated. In particular, data for locations (e.g. each road segment) captured on multiple runs at different times may be aggregated, additional processing performed, and statistical values such as the mean, average, and percentiles, calculated. Other processing may include background correction. For example, background values for particulate matter may be measured on days with rain or a specified portion of the lowest part of the distribution (e.g. the lowest ten percent or twenty percent) may be identified as the background. This background may then be subtracted from the distribution. Other techniques for accounting for the background may be used in other embodiments. In some embodiments, the background may be determined in different ways for different geographic regions (e.g. based on neighborhoods, cities or counties). In some embodiments, the background may be accounted for at only some locations. As part of background subtraction, the sensitivity and/or noise level of sensors may be accounted for. In some embodiments, for example, only sensor data that is greater than the baseline sensitivity and/or noise level of the sensor may be considered. For example, only sensor data that is twice or another multiple of the background and/or noise level (e.g. three, four, five, ten, twenty, or more multiplied by the background and/or noise level) may be used.

Figure 4:
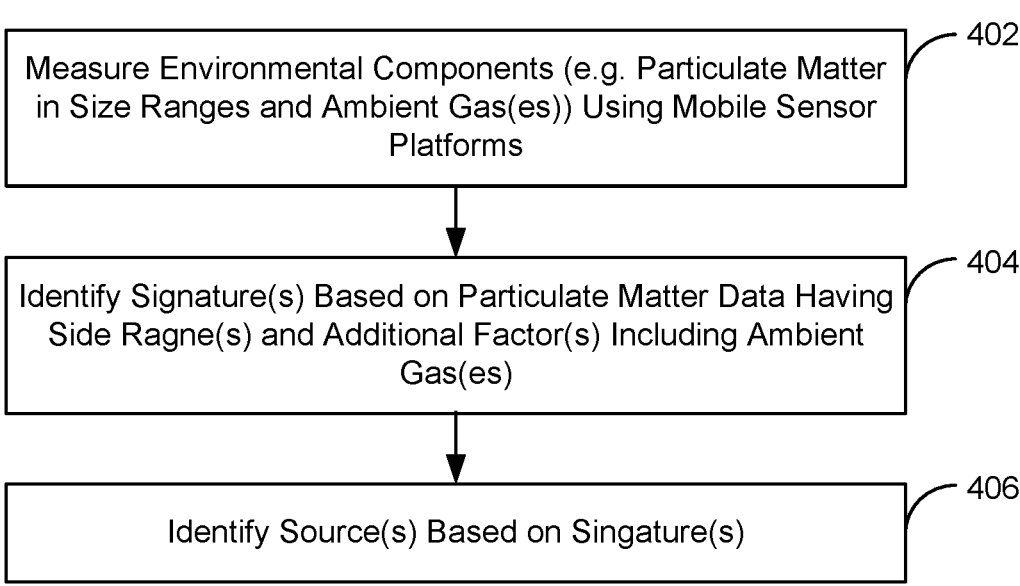
FIG. 4 is a flow chart depicting an embodiment of a method for monitoring environmental quality using signatures utilizing environmental data captured using mobile sensor platforms.

FIG. 4 depicts a method for monitoring air quality using signatures utilizing environmental data captured using mobile sensor platforms and/or stationary sensor platforms, such as mobile sensor platforms 102A, 102B and/or 102C or stationary platform 103. Method 400 is described in the context of system 100, but may be performed using other systems. For clarity, only some portions of method 400 are shown. Although shown in a sequence, in some embodiments, processes may occur in parallel and/or in a different order. Thus, the sensor data described herein may include environmental and/or air quality data including but not limited to particulate matter and various gases.

Environmental components are measured to provide sensor data, at 402. Sensor data, including data related to particulate matter having desired size ranges, is measured using multiple mobile sensor platforms such as mobile sensor platforms 102A, 102B, and 102D and, optionally, stationary platform 103 using method 200, at 402. The sensor data thus includes particulate matter data captured at multiple locations. Further, the particulate matter data may have the hyper-local sensitivity described herein collected at a high-time resolution (e.g. 1 second). In some embodiments, only data for particulate matter having sizes not exceeding 2.5 micrometers is captured, but at 402. In some embodiments, multiple ranges of sizes are captured and can be discriminated. For example, the size range of 2.5 micrometers and below may be broken into various size ranges, each of which captures data for particulate matter within that size range. Data for larger particles may also be captured. For example, size (e.g. diameter or other characteristic size) ranges of <0.3 micrometers, 0.3-0.5 micrometers, 0.5-0.7 micrometers, micrometers, 0.7-1.0 micrometers, 1.0-1.5 micrometers, 1.5-2.0 micrometers, 2.0-2.5 micrometers, and <2.5 micrometers may be discriminated. Thus, in some embodiments, various channels of particulate matter sensors correspond to the size ranges (e.g. 0.3-0.5 micrometers in channel 1, 0.5-0.7 micrometers in channel 2, etc.) Other size ranges, larger and smaller, may be used and/or a different number of size ranges may be used.

In addition to particulate matter, sensor data or other environmental components such as ambient gas(es) is captured at 402. The data for these environmental components is also captured at the hyper-local sensitivity and high time resolution for multiple locations. For example, CO, $CO_2$, NO, $NO_2$, black carbon, organic carbon, $CH_4$, $C_2H_6$, volatile organic compounds (VOCs), total volatile organic compounds (tVOCs), and/or other gases may be measured using method 200, at 402. In some embodiments, 402 includes aggregating, processing (e.g. performing background subtraction), and determining statistical values (e.g. median and/or mean) for the sensor data. In some embodiments, such processing is performed as part of 404.

Signatures are determined based on the particulate matter data and at least one additional factor, at 404. In some embodiments, the signature is determined based on some portion of the size ranges of particulate matter captured and one or more of the ambient gases measured. Thus, other sensor data captured by the mobile sensor platforms may be used in connection with the particulate matter data. Data from other sources including but not limited to other sensor platforms (e.g. stationary sensor platforms), satellite data, geographic data (e.g. map data and/or GPS data), meteorological data (e.g. wind, precipitation, temperature, and/or pressure), radiation data and/or other data may be combined with the particulate matter data to provide a signature for some quantity of interest. The combination may include correlating the particulate matter data with other factor(s), indication of the presence (or absence) of particular components of the environment, amounts (if present) of the particular components of the environment, proximity to geographic features, and/or other mechanisms for determining a relationship between the particulate matter data and the additional factor(s). The correlation may also include comparisons of different size ranges of particulate matter data. For example, the amount (e.g. above background) of particulate matter in the size range 0.3-0.5 micrometers may be compared to the amount of particulate matter in the size ranges of 1.0-2.5 micrometers. The signature indicates the presence or absence of particular sources (e.g. individual sources, source types, and/or areas of spatial impact) and/or other components of the air. For example, the signature may indicate the presence (or absence) of diesel combustion engines, gasoline combustion engines, train or other transportation yards, other sources of particulate matter such as restaurants, salt (or sea spray), traffic (e.g. brake dust), resuspended soil, non-diesel combustion engines, wildfires or fireplaces, and/or other mechanisms by which particulate matter is introduced into the environment.

Source(s) (e.g. individual sources, source types, and areas of high or low spatial impact) are identified based on the signature, at 406. For example, the signature may indicate the presence of a single source (e.g. a passing truck having a diesel combustion engine), areas associated with the signature (e.g. train yards and/or other transportation hubs associated with vehicles using diesel engines), and/or meteorological conditions (e.g. prevailing winds from a coast introducing salt/sea spray to an area).

Thus, using method 400, combinations of features of particulate matter data and other factors may be combined and used to detect various sources (e.g. individual sources/ emitters, source types, and areas of spatial impact such as transportation hubs and/or emitters such as diesel combustion engines). Because data from multiple mobile sensor platforms is used, these sources may be detected in areas where no stationary sensing stations are located. Further, the mobile sensor platforms may be deployed to specific regions of interest. In addition, because hyper-local data is collected and used, the identification of sources signatures may be sensitive to changes on hyper-local scales (e.g. road segments or areas of not more than one hundred and fifty meters in length or diameter, road segments or areas of not more than one hundred meters in length or diameter, or road segments or areas not more than thirty meters in length or diameter). Thus, characterization of sources of particulate matter may be improved.

Figure 5:
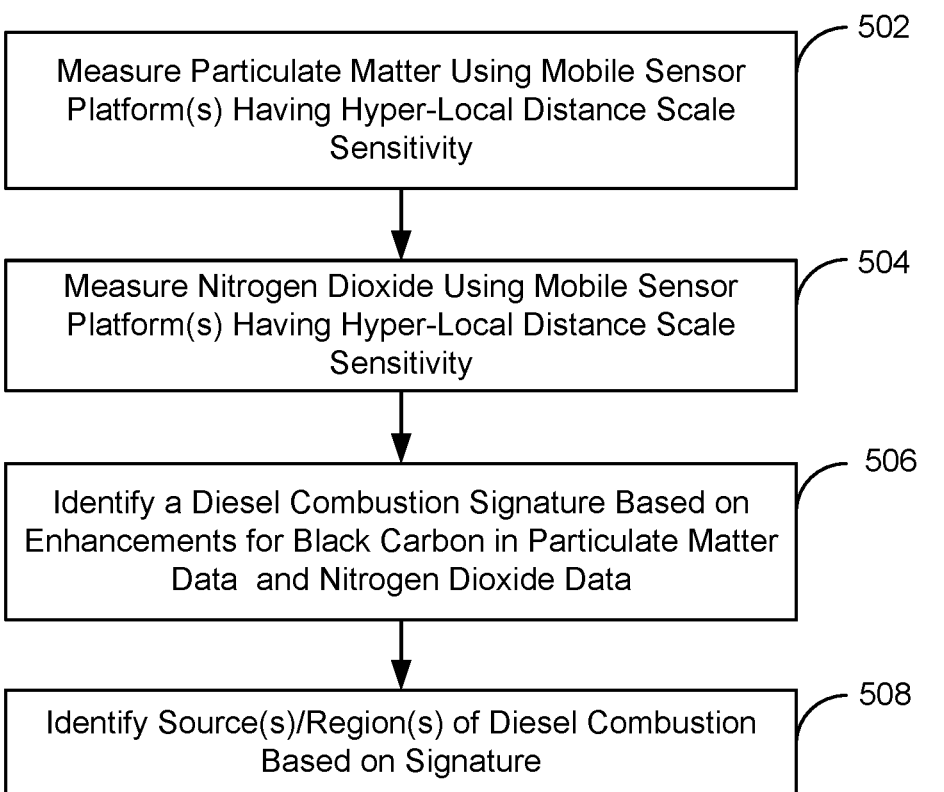
FIG. 5 is a flow chart depicting an embodiment of a method for monitoring environmental quality using diesel signatures utilizing environmental data captured using mobile sensor platforms.

FIG. 5 depicts a method for determining and using diesel combustion signatures utilizing environmental data captured using mobile sensor platforms, such as mobile sensor platforms 102A, 102B and/or 102C. Method 500 is described in the context of system 100, but may be performed using other systems. For clarity, only some portions of method 500 are shown. Although shown in a sequence, in some embodiments, processes may occur in parallel and/or in a different order. Thus, the sensor data described herein may include environmental and/or air quality data including but not limited to particulate matter and various gases.

Particulate matter, including black carbon, is measured using mobile sensor platforms such as mobile sensor platforms 102A, 102B, and 102C of system 100 and, for example, using method 200, at 502. The sensor data thus includes particulate matter data captured at multiple locations. Further, the particulate matter data may have the hyper-local sensitivity collected at high-time resolution, as described herein. In some embodiments, only data for particulate matter having sizes not exceeding 2.5 micrometers is captured at 502. In some embodiments, particulate matter of larger sizes (e.g. 2.5-10 micrometers) may also be captured. Thus, particulate matter of other larger or smaller sizes can be used (e.g. PM10, PM20, PM0.5). In some embodiments, multiple ranges of sizes are captured and can be discriminated. For example, the size ranges described above may be used. Thus, the particulate matter data may have a detection threshold that is greater than zero micrometers. In some embodiments, other smaller and larger size ranges may be used. The particulate matter detected includes black carbon. In some cases, black carbon may be considered to be particulate matter having a size of 2.5 micrometers or below. In some embodiments, black carbon may be considered to be only with a subset of particles in this size range (<0.5 micrometers). Thus, a portion of the particulate matter data may be associated with black carbon. For example, freshly emitted black carbon may be considered to have a size of less than 0.3 micrometers. While a particulate matter sensor may have a lower threshold of less than 0.3 micrometers, black carbon may be measured by a different sensor that measures particles down to almost zero micrometers using a different method of measurement. For example, black carbon may be measured by a sensitive method using light absorption after particles are collected on a filter, which allows the detection of black carbon to be measured at 502 by the absorption method. Other techniques for measuring particulate matter, including measuring black carbon, may be used in other embodiments. Thus, in some embodiments, particulate matter may be measured using different techniques at 502. For example, black carbon may be measured using the absorption method, while particulate matter having sizes of 0.3 micrometers to ten micrometers or more may be measured using other technique(s).

Nitrogen dioxide is measured using the mobile sensor platforms, at 504. In some embodiments, 504 includes measuring nitrogen dioxide using stationary sensor platforms. In some embodiments, other components of the environment may be measured at 504. For example, CO, $CO_2$, NO, VOCs, tVOCs, and/or other gases may be measured at 504. Further, the nitrogen dioxide and other data may have the hyper-local sensitivity described herein. The sensor data captured by the mobile sensor and other platforms for method 500 thus includes particulate matter data and nitrogen dioxide data (and/or other ambient gas data) captured at multiple locations. The specific locations at which particulate matter data (e.g. black carbon data) and nitrogen dioxide data are captured may be the same or different locations (e.g. the same or different road segments). However, the black carbon and nitrogen gas data may be associated with the same or nearby hyper-local locations. For example, a particular nitrogen dioxide data point may be from the same road segment, a nearest neighbor road segment or a next-nearest neighbor road segment from a corresponding black carbon data point. The times and locations of data captured are similar for nitrogen dioxide data and the associated black carbon data. In some embodiments, the nitrogen dioxide data captured at 504 and associated black carbon data captured at 502 are captured at substantially the same time. For example, the measurements may be made using the same mobile sensor platform on the same run. In general, the nitrogen dioxide data and the associated black carbon data captured by the same mobile sensor platform are measured at the same time (e.g. within one second, five seconds or ten seconds of each other) and at the same location (e.g. the same road segment). Thus, the data captured at 502 and 504 are temporally and spatially correlated. The data set as a whole may also include data from multiple mobile sensor platforms captured on multiple runs. In such embodiments, a particular nitrogen dioxide data point and a particular corresponding black carbon data point used in method 500 may be captured by the same mobile sensor platform on the same run (at approximately the same time and location). In some embodiments, however, nitrogen dioxide data and black carbon points may be captured using different mobile sensor platforms and/or on different runs. However, individual data points within the sensor data are generally desired to be captured within a particular time window (e.g. on the same day, within an hour, etc.). Thus, although the complete data sets for the nitrogen dioxide data and the particulate matter data may be captured over a longer period of time (e.g. a month, a quarter, or a year) and over a larger area (e.g. a city, a county, or a state), such that paired individual nitrogen dioxide and individual particulate matter (e.g. black carbon) data points are desired to be temporally and spatially correlated and/or collected at the same time. The data from multiple sensor platforms and multiple runs may be aggregated and processed. In some embodiment, 502 and 504 are performed at substantially the same time during runs of mobile sensor platforms in method 200.

The diesel combustion signature is determined based on the portion of the particulate matter data corresponding to black carbon, the nitrogen dioxide data and/or other relevant ambient gas(es) and/or other particulate matter data, at 506. More specifically enhancements in the portion of the particulate matter data corresponding to black carbon, the nitrogen dioxide data, and/or other relevant ambient gases/particulate matter correspond to the presence of diesel combustion source(s). An enhancement may include features (e.g. increases or peaks; decreases or valleys; values that are a multiple such as two, three, four, five, ten, or more above background) in the statistical aggregation of and/or ratios in the data. Thus, at 506 an enhancement (e.g. peak or amount above background) in the particulate matter data for black carbon in combination with an enhancement (e.g. peak or amount above background) in the nitrogen dioxide data corresponds to the presence of diesel combustion and, therefore, the diesel combustion signature.

In some embodiments, other size ranges for particulate matter may be used in 506 in addition to black carbon. For example, particulate matter having a size range of less than 0.5 micrometers (e.g. in the 0.3-0.5 micrometer size range described above) may be used in determining the diesel combustion signature. In some embodiments, the particulate matter data in this size range compared to particulate matter in other size ranges may be used in determining the diesel combustion signature. In some embodiments, the black carbon measured may be compared with particulate matter in various size ranges. For example, the amount of particulate matter having a size less than 0.5 micrometer (e.g. 0.3-0.5 micrometer) being significantly greater than (e.g. twice, thrice, five multiplied by, ten multiplied by or more) the amount of particulate matter in the size range of 1.0-2.5 micrometers may be considered indicative of diesel combustion. Thus, this ratio in combination with the amount of nitrogen dioxide and black carbon may be used in determining the diesel combustion signature.

In some embodiments, additional environmental constituents may be used in the diesel combustion signature. For example, CO, $CO_2$, NO, total volatile organic compounds (tVOCs), and ratios between $NO_2$, CO, $CO_2$, NO, black carbon, and/or tVOCs may be used in addition to particulate matter data of various size ranges, nitrogen dioxide data, and black carbon data. In general, geographic data (e.g. GPS or other data indicating the hyper-local locations of the particulate matter data and nitrogen dioxide data) is also used in determining the signature, at 506. The diesel combustion signature includes a correlation between constituents of the environment associated with diesel combustion (e.g. a correlation between higher amounts of particulate matter in the desired size range, black carbon, nitrogen dioxide, a higher ratio of nitrogen dioxide to carbon dioxide; and/or other ratios to other gases, particulate matter in the desired size range, black carbon, VOCs, and/or tVOCs) for the same geographic area. For example, various diesel combustion signatures may be determined based on the percentiles of particulate matter in the desired size range, nitrogen dioxide, black carbon and/or other environmental component(s), the percentiles of such environmental components being above a threshold (e.g. for particulate matter in the desired size range, nitrogen dioxide, black carbon, and/or other environmental components), or some other measure of the presence of such constituents. In some embodiments, therefore, determining the diesel combustion signature may further include determining, based on the black carbon data, the nitrogen dioxide data, other particulate matter data, black carbon median values, nitrogen dioxide median values, and/or other particulate matter median values for the locations (e.g. road segments, cells, or collections of road segments). In some embodiments, other statistical measures of black carbon, nitrogen dioxide, particulate matter in the desired size range, and/or other components of the environment may be used. For example, the average particulate matter data for a location, the average nitrogen dioxide data for a location, the average black carbon data for the location, the total amount of particulate matter in the desired size range detected within a particular time window for a location, the total amount of nitrogen dioxide data collected in a particular time window for a location may be used and/or the total amount of black carbon data collected in a particular time window may be used. In some embodiments, determining the diesel combustion signature at 506 may include locating peaks for black carbon, nitrogen dioxide, particulate matter in a desired size range and/or or other relevant ambient gas(es).

Diesel combustion source(s) are identified based on the signature, at 508. For example, if a particular geographic area (e.g. one or more road segments and/or cells) has median black carbon data values in the top $10^{th}$ percentile for the black carbon data (i.e. in the $90^{th}$ percentile and above) and the particular geographic area has a median nitrogen dioxide data in the top $10^{th}$ percentile (i.e. in the $90^{th}$ percentile and above) for the nitrogen dioxide data, the region may be identified as having a high impact of diesel combustion. In some embodiments, this determination is also made based on the particular geographic area having a median particulate matter data for the desired size range in the top $10^{th}$ percentile (i.e. in the $90^{th}$ percentile and above) and/or other relevant ambient gas(es) having median values in such percentile ranges. In some embodiments, having black carbon data in the desired range, nitrogen dioxide data, and (in some embodiments) black carbon data and/or other ambient gas data in the $60^{th}$ to $90^{th}$ percentile (e.g. particulate matter data for less than 0.5 micron in the above $60^{th}$ percentile and nitrogen dioxide and black carbon in the $90^{th}$ percentile) is considered to be a medium impact region of diesel combustion. Thus, sources corresponding to various diesel signatures may be associated with differing percentiles of particulate matter and nitrogen dioxide and/or other relevant ambient gas. This spatial correlation between diesel signatures and regions (e.g. the identification of sources) may allow the classification of the sources as being truck depot(s), truck route(s), warehouse(s), bus depots, and the like. Other embodiments may include enhancements of nitrogen dioxide data, black carbon data, particular matter data for less than 0.5 micrometers, and/or other relevant ambient gas. For example, these ranges or enhancements may identify transportation hubs (e.g. diesel truck routes or depots) that are sources of diesel combustion pollutants. In some embodiments, other geographic and/or meteorological and/or meteorological data may be incorporated. For example, known locations of diesel truck routes may be used along with black carbon data, nitrogen dioxide data and, in some embodiments, other relevant ambient gas(es) and/or particulate matter data having a size range of less than 0.5 micron to identify sources. In another example, a source in the form of an area of spatial impact may be identified with meteorological data, geographic information (e.g. the location of a railyard, port, warehouse, or airport) and environmental data. Areas impacted by the railyard (e.g. an area north of the railyard) may be identified using environmental data (e.g. the presence of black carbon and nitrogen dioxide) and the meteorological data (e.g. a wind blowing from the south). Further, temporal correlation between the diesel signatures and sources (e.g. the diesel signature is present for a geographic region at only particular times) may also allow for sources such as truck routes to be distinguished from sources such as truck depots. In some embodiments, the diesel signature may also be correlated with VOCs arising from combustion. Thus, sources of combustion VOCs may also be identified. In some embodiments, other thresholds, and/or other combinations of factors (e.g. or other relevant ambient gases or particles size ranges larger or smaller than described) may be used to identify diesel combustion sources/region(s)/spatial impact and/or or to determine the diesel combustion signature.

Thus, using method 500, combinations of features of black carbon data, the presence of nitrogen dioxide, and in some embodiments particulate matter in the desired size range and/or other relevant ambient gas(es) may be used to identify a signature for diesel combustion and detect various diesel combustion sources. Geographic and/or meteorological data may be incorporated. Because data from mobile sensor platforms is used, these sources may be detected in areas where no stationary sensing stations are located. Further, the mobile sensor platforms may be deployed to specific regions of interest. In addition, because hyper-local data is collected and used, the identification of sources and signatures may indicate variations down to hyper-local scales (e.g. road segments or areas not more than one hundred meters in length or diameter, or road segments or areas not more than thirty meters in length or diameter). Thus, not only may areas of spatial impact having characteristic lengths on the order of one thousand feet, two thousand feet, or more be identified, but variations within such regions indicated. Thus, characterization of sources of diesel combustion may be improved.

Figure 6:
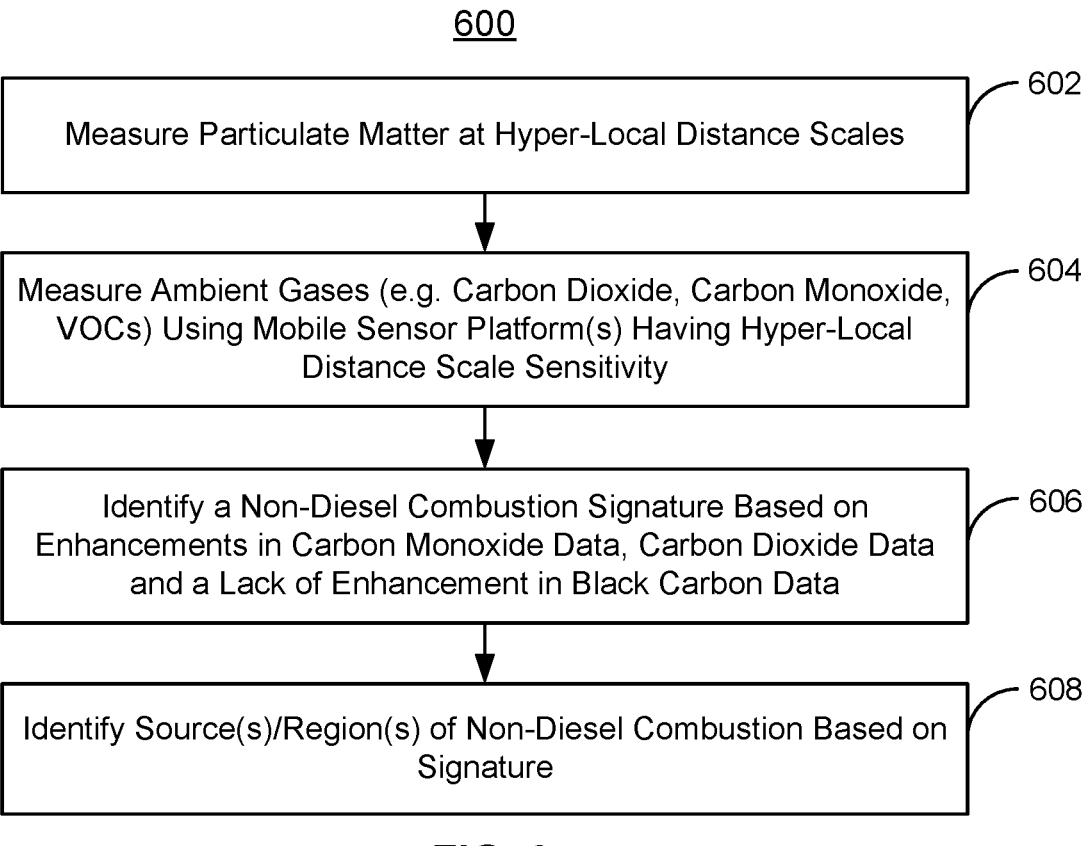
FIG. 6 is a flow chart depicting an embodiment of a method for monitoring environmental quality using diesel signatures utilizing environmental data captured using mobile sensor platforms.

In some embodiments, a non-diesel combustion signature may include carbon monoxide, carbon dioxide, VOC, tVOC and/or other relevant ambient gases. FIG. 6 depicts a method for determining and using non-diesel combustion signatures utilizing environmental data captured using mobile sensor platforms, such as mobile sensor platforms 102A, 102B and/or 102C. Method 600 is described in the context of system 100, but may be performed using other systems. For clarity, only some portions of method 600 are shown. Although shown in a sequence, in some embodiments, processes may occur in parallel and/or in a different order. Thus, the sensor data described herein may include environmental and/or air quality data including but not limited to particulate matter and various gases.

Particulate matter having desired size ranges is measured using mobile sensor platforms such as mobile sensor platforms 102A, 102B, and 10C of system 100 and, for example, using method 200, at 602. In some embodiments, 602 is analogous to 502. Thus, black carbon as well as other types of particulate matter may be measured at 602. The sensor data thus includes particulate matter data captured at multiple locations. Further, the particulate matter data in one or multiple size ranges may have the hyper-local sensitivity described herein. The particulate matter data captured at 602 includes the size ranges described with respect to methods 400 and 500. Carbon monoxide, carbon dioxide, tVOC or VOC, and/or other relevant ambient gases are measured using the mobile sensor platform, at 604. The sensor data thus includes particulate matter data in one or multiple size ranges captured at multiple locations that are generally the same as or correlated with (but may be different from) the locations for 602. Similarly, the particulate matter data captured at 602 is generally at measured substantially the same time as (e.g. within one second, five seconds, or ten seconds) as the data for nitrogen dioxide and/or other relevant ambient gas(es). Thus, the data captured at 602 and 604 are temporally and spatially correlated. Further, the data related to carbon monoxide, carbon dioxide, tVOC, VOC, and/or other ambient gases may have the hyper-local sensitivity and fine temporal sensitivity described herein. In some embodiments, 604 is analogous to 504.

The non-diesel combustion signature is determined based on enhancements (e.g. peaks, elevated levels, valleys, or reduced levels) in the carbon monoxide data, the carbon dioxide data, the tVOC, VOC data, and/or data related to other relevant ambient gases, at 606. The non-diesel combustion signature is also determined at 606 based on a lack of enhancement in black carbon data. A lack of enhancement may be considered to be a valley (i.e. a specific type of enhancement) and/or a lack of an amount above background. For example, for black carbon, a lack of enhancement may include data on the order of background readings. This may correspond to a valley in comparison to nearby regions (e.g. a nearby high diesel impact area). In general, geographic data (e.g. GPS or other data indicating the hyper-local locations of the particulate matter data, carbon dioxide data, carbon monoxide data, tVOC data, VOC data and/or other ambient gas data) is also used in determining the signature at 606. The non-diesel combustion signature includes higher particulate matter data in certain range(s) (e.g. a higher ratio than other size range(s) and/or higher absolute values or increases above background), higher carbon monoxide data, higher carbon dioxide data, higher VOC, higher tVOC, and a low ratio of black carbon to carbon monoxide or carbon dioxide for the same geographic area. In some embodiments, median values of the data for each location are used in 606. In some embodiments, therefore, 606 includes determining the median values for the sensor data for the locations (e.g. road segments, cells, or collections of road segments). In some embodiments, other statistical measures of the sensor data may be used. For example, the average (mean) amount(s) for a particular location and/or the total amount(s) within a particular time window for a particular location may be used. In some embodiments, determining the non-diesel combustion signature at 606 may include locating peaks for particulate matter data in the desired size range, peaks for carbon monoxide data, peaks for carbon dioxide data, peaks for VOC data, peaks for tVOC data and/or the low ratio of black carbon to carbon monoxide or carbon dioxide. Such peaks may be considered a statistical measure of the sensor data.

Non-diesel combustion source(s)) including individual sources, source types, and/or areas of spatial impact(s) including individual sources, source types, and/or areas of spatial impact(s) are identified based on the signature, at 608. In some embodiments, the percentiles for particulate matter, carbon monoxide, and carbon dioxide described herein are used. In some embodiments, other geographic data, meteorological data, and/or other data (e.g. other gases) may be incorporated. As such, 608 may be analogous to 508. For example, known locations of gasoline-powered transportation corridors or hubs may be incorporated into the identification of non-diesel combustion sources/regions/spatial impacts of sources/source regions. Metrology may be incorporated at known locations or identified locations or identified locations to the spatial extent of the non-diesel combustion sources from sources/source regions.

Thus, using method 600, combinations of features of black carbon data, particulate matter data corresponding to desired size ranges (e.g. less than 0.5 micrometers) and the presence of carbon monoxide, carbon dioxide, tVOC, VOC, and/or other relevant ambient gases may be used to identify a signature for non-diesel combustion and detect various non-diesel combustion sources. Because data from mobile sensor platforms is used, these sources may be detected in areas where no stationary sensing stations are located. Further, the mobile sensor platforms may be deployed to specific regions of interest. In addition, because hyper-local data is collected and used, the identification of sources/regions/spatial impact and signatures may indicate variations on hyper-local scales (e.g. road segments or areas more than one hundred meters in length or diameter, or road segments or areas not more than thirty meters in length or diameter) in addition to identifying larger regions of spatial impact. Thus, characterization of sources of non-diesel combustion may be improved.

Using method 400, 500, and/or 600 diesel and non-diesel combustion may be discriminated from other sources of particulate matter in the same size range or different size ranges. For example, diesel combustion may be discriminated from woodsmoke (e.g. wildfires, residential fireplaces, and/or other wood fires) or restaurants by utilizing particulate matter data in combination with data from other relevant gas(es). In some embodiments, restaurants or other sources of particulate matter may be separated and identified using method 400, 500, and/or 600. In some embodiments, other pollutants, other correlations and/or thresholds may be used. For example, the change in black carbon, nitrogen dioxide, and/or other particulate matter over time (e.g. based on times of day, days of the week, time of year, or progression of days, months or years) for particular location(s) (e.g. road segment(s)) may be used to identify a diesel combustion signature and/or source. In addition, in some embodiments, types of traffic may be discriminated using method(s) 400, 500, and/or 600. For example, the presence of a higher amount of black carbon, a higher amount of nitrogen dioxide, and/or larger amounts of particulate matter in the desired size ranges and/or other ambient gas(es) indicate a diesel combustion source, while the presence of less black carbon, a lower amount of nitrogen dioxide and a high CO to $CO_2$ ratio may indicate the presence of other types of combustion engines. Similarly, the presence of particulate matter in other size ranges (e.g. more particulate matter greater than 1.5 micrometers or the ratio of the particulate matter greater than 1.5 micrometers in size to the particulate matter in the less than 0.5 micrometer or 0.3-0.5 micrometer size range being much greater than one) may be indicative of other sources of particulate matter, such as road dust or sea spray.

Figure 7:
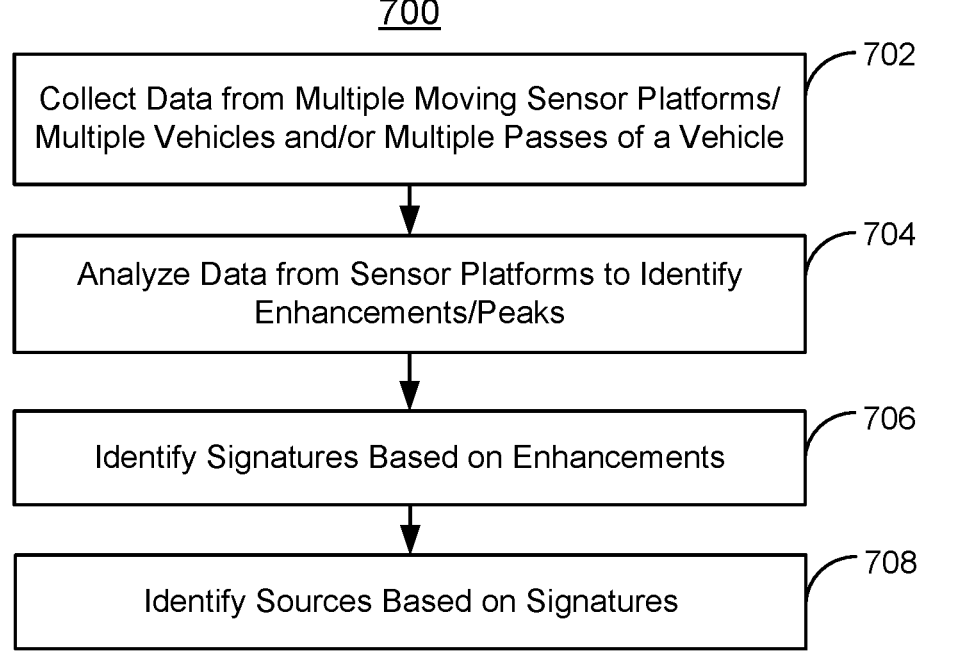
FIG. 7 is a flow chart depicting an embodiment of a method for monitoring environmental quality using signatures utilizing environmental data captured using mobile sensor platforms.

For example, FIG. 7 depicts a method for determining and using signatures utilizing environmental data captured using mobile sensor platforms, such as mobile sensor platforms 102A, 102B and/or 102C. Method 700 is described in the context of system 100, but may be performed using other systems. For clarity, only some portions of method 700 are shown. Although shown in a sequence, in some embodiments, processes may occur in parallel and/or in a different order. Thus, the sensor data described herein may include environmental and/or air quality data including but not limited to particulate matter and various gases, geographic, temporal, and meteorological data. Data having the desired sensitivity (i.e. both for sensor sensitivity and hyper-local distance sensitivity) are gathered, at 702. 702 may include gathering black carbon data, other particulate matter data over a size range (e.g. 0.3 micrometer through ten micrometers), nitrogen dioxide data, nitrogen monoxide data, carbon monoxide data, carbon dioxide data, black carbon data, organic carbon data, VOCs, tVOC, other relevant ambient gas data, and/or other data such as geographic data and meteorology data. The data is gathered using mobile sensor platforms such as mobile sensor platforms 102A, 102B, and 102C of system 100 and, for example, using method 200, at 702. In some embodiments, 702 includes processes analogous to 402, 502, 602, 504, and 604. Thus, background subtraction, statistical aggregation of the sensor data, and/or other data processing may be performed. The data are analyzed to find enhancements, such as peaks, valleys, and/or the absence of environmental constituents at 704. Signatures and sources are identified at 706 and 708. In some embodiments, 706 and 708 are analogous to 404 and 406, 506 and 508, and/or 608 and 610.

Using method 700, if enhancements in the particulate matter for portions (or all) of the size range measured an ambient gas data may are detected and used for the signature, various conclusions may be drawn. For example, enhancements in black carbon (e.g. a peak in black carbon) and nitrogen dioxide data (e.g. a peak in nitrogen dioxide) possibly in connection with an absence of a peak in carbon monoxide may be used for the diesel signature at a particular location. Thus, vehicles that utilize diesel combustion may be able to be identified at the particular location or by a particular mobile sensor platform as it moves through its route. For the same or similar enhancements in black carbon, nitrogen dioxide, and/or other component(s) of the environment, the enhancements may be correlated with geographic features such as railyards or shipping ports, meteorological data such as temperature and wind data, and/or temporal data such as wildfire events. This correlation may be performed as part of source identification at 708. In such embodiments, wildfires (temporal correlation with wildfire events and/or meteorological data such as wind direction from the wildfire event), railyards or shipping ports (geographic data and meteorological data such as wind direction from the airport), and sources of diesel combustion may be separately identified. Thus, more information related to the environment may be obtained and mitigation measures, if any, may be proposed.

In another example, vehicles burning regular gasoline do generally not emit black carbon, emit a lower amount of nitrogen dioxide based on fuel burned and a higher amount of carbon monoxide. Thus, using method 700 (e.g. in a manner analogous to method 600), a signature for a regular gas burning vehicle may be determined at 706 through enhancements that include the absence of a peak in black carbon, a reduction in the height (or absence) of a nitrogen dioxide peak and a peak in carbon monoxide (or a peak in the ratio of carbon monoxide to carbon dioxide) and/or a peak in VOC and tVOC. Using this non-diesel combustion signature, sources of gasoline combustion may be detected. Part of detection of the source of non-diesel combustion may include associating the regions indicated by the enhancements with geographic features such as freeways and/or temporal correlation with expected traffic patterns such as rush hours. In some embodiments, the number of non-diesel combustion vehicles passing the mobile sensor platforms may be identified through repeated detection of the non-diesel combustion signature over time from data taken by each mobile sensor platform. In such embodiments, the extent of diesel combustion vehicles identified by the mobile sensor platforms may be compared to the extent of non-diesel combustion vehicles identified for various road segments and/or routes traversed for particular time windows. Thus, traffic patterns (e.g. diesel combustion vs. non-diesel combustion vehicles) for road segments may be determined.

In some embodiments, signatures other than for diesel combustion and non-diesel combustion may be determined.

Figure 8:
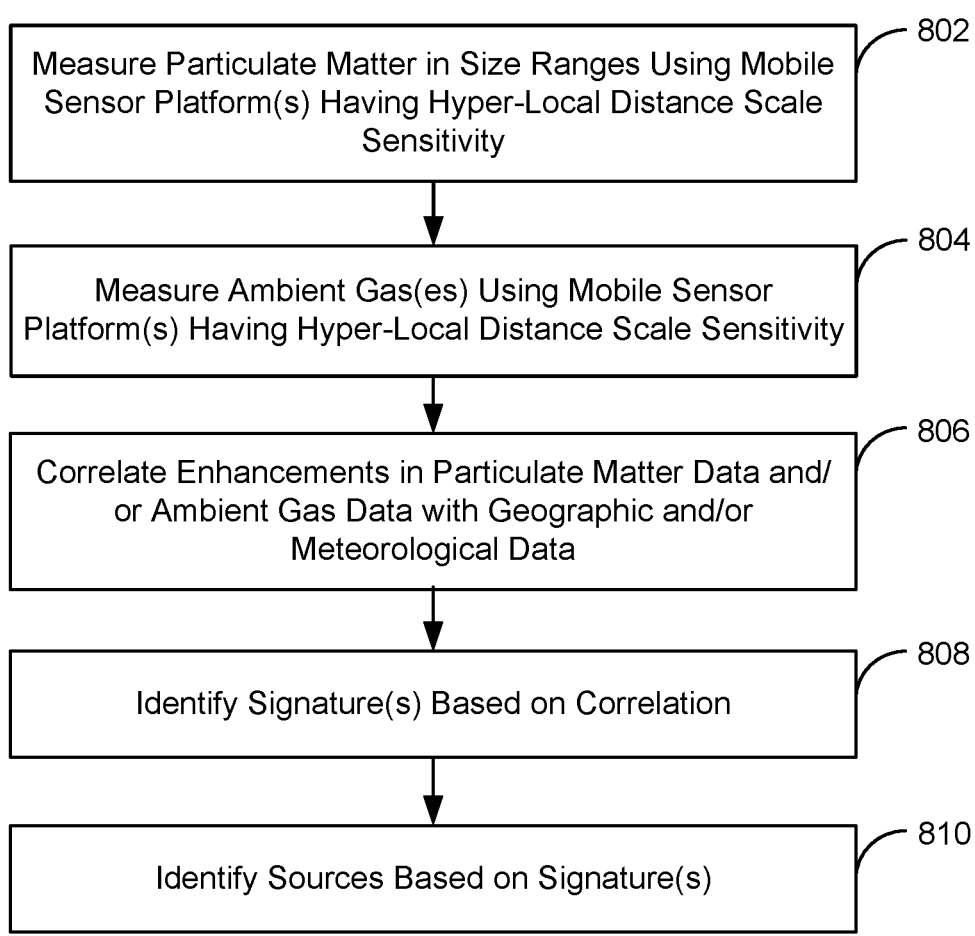
FIG. 8 is a flow chart depicting an embodiment of a method for monitoring environmental quality using signatures utilizing environmental data captured using mobile sensor platforms.

For example, FIG. 8 depicts a method for determining signatures utilizing environmental data captured using mobile sensor platforms, such as mobile sensor platforms 102A, 102B and/or 102C of system 100. Method 800 is described in the context of system 100, but may be performed using other systems. For clarity, only some portions of method 800 are shown. Although shown in a sequence, in some embodiments, processes may occur in parallel and/or in a different order. Thus, the sensor data described herein may include environmental and/or air quality data including but not limited to particulate matter and various gases.

Particulate matter, including black carbon, is measured using mobile sensor platforms such as mobile sensor platforms 102A, 102B, and 102C of system 100 and, for example, using method 200, at 802. In some embodiments, 802 is analogous to 502. The particulate matter data thus includes particulate matter data captured at multiple locations. Further, the particulate matter data may have the hyper-local sensitivity and be highly time-resolved, as described herein. Other data may also be captured at 802. Data may also be processed at 802. For example, the statistical aggregation described herein may be performed as part of 802.

Ambient gas(es) and organic carbon are measured using mobile sensor platforms such as mobile sensor platforms 102A, 102B, and 102C of system 100, at 804. For example, CO, $CO_2$, NO, $NO_2$, VOCs, tVOCs, and/or other gases may be measured at 804. Further, the ambient gas, black carbon, organic carbon, and other data may have the hyper-local sensitivity described herein. The ambient gas, black carbon, or organic carbon data may also be highly time-resolved. The sensor data captured by the mobile sensor and other platforms for method 800 thus includes particulate matter data having a size range (e.g. from less than 0.3 micrometer or less than 0.5 micrometer through 10 micrometer) and ambient gas, black carbon, and organic carbon data captured at multiple locations. In some embodiments, 802 and 804 are analogous to 402; 502 and 504; 602, 604, and 606; and 702 and 704.

At 806, the enhancements in the data captured at these locations is correlated with data from other data sources, such as data relating to geographic areas (e.g. from a map) and/or meteorological data (e.g. data related to meteorological conditions such as temperature, wind speed and direction, pressure, and/or precipitation that may come from satellites, historical data, or other sources). In such embodiments, signature(s) are determined based on the correlation at 808 and source(s) identified, at 810.

For example, geographic data such as the presence and proximity of coastlines or bodies of water and meteorological data such as prevailing wind speed and direction may be correlated with enhancements in particulate matter data having larger sizes and enhancement(s) in ambient gas data, at 806. The enhancement(s) in particulate matter data may be a peak in particulate matter having a size range of 1-2.5 micrometers, a peak in particulate matter having a size range of 2.5-7 micrometers, a peak in particulate matter having a size range of 2.5-10 micrometers, a peak in some combination of these size ranges and/or the lack of a peak/a valley in a ratio of particulate matter of a lower size range such as less than 0.5 micrometers or 0.3-0.5 micrometers to particulate matter having a larger size such as 1-2.5 micrometers. In some embodiments, the enhancement(s) may include the absence of the peak in the ratio in combination with the peak in larger sizes (e.g. 2.5-10 micrometers). The enhancement in ambient gas data may be the lack of peaks in carbon monoxide, nitric oxide, and/or carbon dioxide and/or other gases at the same locations and/or times. Such enhancement(s) are correlated with the geographic data and the meteorological data. This correlation may be used to determine a sea salt signature, at 808. The enhancement(s) in larger-sized particulate matter and ambient gas(es) combined with proximity to a body of saltwater close to and/or upwind from the location of the enhancement(s) determine a sea salt signature. Thus, a sea spray source may be identified based on the sea salt signature, at 810. In some embodiments, the enhancement(s) in larger-sized particulate matter in combination with the enhancement(s) in ambient gas data may not be concurrent with proximity to a body of salt water. In such embodiments, the correlation may provide a construction dust signature at 808. A temporal correlation with construction times and an additional geographic correlation such as known construction sites may also be used.

In some embodiments, an enhancement in particulate matter in a desired size range and enhancement(s) in ambient gas data may be correlated with the speed of the mobile sensor platforms. The enhancement(s) in particulate matter data may be a peak in mid- to larger-sized particulate matter. For example, the enhancement(s) may include a peak in particulate matter having a size range of 1-2.5 micrometers, a peak in particulate matter having a size range of 2.5-7 micrometers, a peak in some combination of these ranges and/or the lack of a peak/a valley in a ratio of particulate matter of a lower size range such as less than 0.5 micrometers or 0.3-0.5 micrometers to particulate matter having a larger size such as 1-2.5 micrometers. The enhancement in ambient gas data may be the peaks in carbon monoxide, nitric oxide, and/or carbon dioxide or other gases at the same locations and/or times. Such enhancement(s) are correlated with the speed of the mobile sensor platforms, at 806. For speeds much less than the speed limit of a region (e.g. approaching zero or at least decreasing speeds), the signature determined at 808 may be a brake dust signature. An enhancement in particulate matter at larger sizes (e.g. <1.5 micrometers) is correlated with vehicle speed, then at 808 a road dust signature may be determined. The sources may be identified as the vehicle carrying the mobile sensor platform, surrounding vehicles, or regions of the freeways, at 810. A temporal correlation at 806 may also be used to provide a signature for high traffic congestion at 808. Thus, expected traffic congestion patterns may be determined as time-varying sources, at 810. Similarly, signatures for other sources of particulate matter, such as restaurants or wood fires, may be determined and the sources identified using method 400 and/or 800. In some embodiments, other sensor data in addition to or in lieu of geographic and/or meteorological data may be used to determine other non-diesel relevant signatures. For example, volatile organic compounds (VOCs) may be measured, and the VOC data analyzed and utilized in connection with particulate matter and other data to identify and map various sources of pollutants and other components of the environment. Thus, using signatures for various sources of pollutants and/or other components of the environment, such sources may be identified, mapped, analyzed and issues related to the sources mitigated.

FIG. 9 is a block diagram illustrating an embodiment of method 900 for monitoring the environmental data using signatures and environmental data captured using mobile sensor platforms, such as mobile sensor platforms 102A, 102B and/or 102C. Method 900 is described in the context of system 100, but may be performed using other systems. For clarity, only some portions of method 900 are shown. Although shown in a sequence, in some embodiments, processes may occur in parallel and/or in a different order. Thus, the sensor data described herein may include environmental and/or air quality data including but not limited to particulate matter, black carbon, organic carbon, and various ambient gases.

Particulate matter having desired size ranges and other environmental and/or air quality data is measured using mobile sensor platforms such as mobile sensor platforms 102A, 102B, and 102C ins system 100 and, for example, using method 200, at 902. In some embodiments, 902 is analogous to 402 and 502. The particulate matter data and other environmental and/or air quality data thus includes data captured at multiple locations. Further, the particulate matter data and other environmental and/or air quality data may have the hyper-local sensitivity and be highly time resolved, as described herein. Other data may also be captured at 902. Further, the data may be processed, including accounting for background signals. Thus, for example, the enhancement of particulate matter data over background may be determined.

The amount or concentrations of particulate matter in various size ranges and other environmental and/or air quality data are determined, at 904. For example, means or medians of particulate matter in a size range of 0.5 micrometer through 1 micrometer may be determined over time for the hyper-local, highly time resolved data. Peaks, valleys, and/or other features in these averages may be determined at 904.

The particulate matter data and other environmental and/or air quality data and/or features thereof are correlated to temporal factors, at 906. In some embodiments, the enhancements over background, absolute amounts, and/or concentrations of the particulate matter in certain size ranges and other environmental and/or air quality data may be compared to daily, monthly, yearly, or seasonal averages at 906. For example, particulate matter data and other environmental and/or air quality data for a particular day may be compared to the seasonal average, the average for the year, or the multi-year average for the particular day (e.g. the average concentration of particulate matter in the size range for September first of year 6 may be compared to the average of September first for years 1 through 6). The correlation may also be made to averages of temperature, precipitation, wind pressure, and/or other characteristics for the month, season, or year.

A temporal particulate matter signature or signatures for other environmental and/or air quality data can be determined based on the correlations, at 908. For example, peaks (or valleys) in particulate matter in the size range or other environmental and/or air quality data that are correlated with higher than average rainfall may be identified with a "clean day" (as opposed to a "high pollution" day) signature. Sources and/or characteristics of the region may then be identified based on the correlation, at 910.

Using method 900, longer term characteristics in the presence of particulate matter and other environmental and/or air quality data and/or other constituents of the environment may be determined and tracked. Similarly, characteristics that are spatially and/or temporally invariant may be determined. As such, longer term characteristics of the environment may be determined and mitigation procedures and/or a regulatory framework identified.

Although the foregoing embodiments have been described in some detail for purposes of clarity of understanding, the invention is not limited to the details provided.

There are many alternative ways of implementing the invention. The disclosed embodiments are illustrative and not restrictive.

What is claimed is:

1. A method for monitoring air quality, comprising:

measuring a plurality of environmental components at a plurality of locations using a plurality of mobile sensor platforms to provide sensor data, the environmental components including particulate matter having a size range and a plurality of ambient gases, the sensor data including particulate matter data having the size range and ambient gas data captured at the plurality of locations, wherein the ambient gas data includes nitrogen dioxide data, wherein the particulate matter data includes black carbon data;

determining a signature based on the particulate matter data including the size range and at least one additional factor, the at least one additional factor including the ambient gas data, wherein the at least one additional factor further includes a temporal factor indicating a wildfire, wherein the signature is a diesel combustion signature, and wherein the determining of the signature includes:

determining the diesel combustion signature based on the nitrogen dioxide data indicating an ambient gas enhancement in nitrogen dioxide and the black carbon data indicating an enhancement in black carbon, wherein the temporal factor indicates a presence of the wildfire; and in response to a determination that the temporal factor indicates the presence of the wildfire, determining a wildfire signature;

identifying a source based on the signature, comprising:

identifying at least one diesel combustion source based on the diesel combustion signature; and performing a mitigation measure based on pollutants output by the identified source.

2. The method of claim 1, wherein a portion of the particulate matter has a size range of less than 0.5 micrometer, the determining the signature further includes:

determining the diesel combustion signature based on a first enhancement in a first ratio of nitrogen dioxide to carbon dioxide, a second enhancement in a second ratio of black carbon to carbon dioxide, and a third enhancement in a third ratio of the portion of the particulate matter data to carbon dioxide.

3. The method of claim 1, wherein the source is an area of spatial impact, the diesel combustion signature indicating the area of spatial impact has higher or lower diesel emissions than another region.

4. The method of claim 1, wherein the signature is a non-diesel combustion signature, wherein the plurality of ambient gases includes carbon monoxide, carbon dioxide, and volatile organic compounds (VOC), wherein the ambient gas data includes carbon monoxide data, carbon dioxide data, and VOC data, and wherein the determining the signature includes:

determining the non-diesel combustion signature based on the carbon dioxide data and the carbon monoxide data indicating an enhancement in a ratio of the carbon monoxide to the carbon dioxide, the VOC data indicating a VOC enhancement, and a lack of a particulate matter enhancement corresponding to black carbon; and wherein the identifying further includes identifying at least one non-diesel combustion source based on the diesel combustion signature.

5. The method of claim 1, wherein the at least one additional factor includes at least one of a geographic area, mobile platform speed, or meteorological data, and wherein the determining the signature further includes at least one of:

determining a sea salt signature based on a portion of the particulate matter data having a size range of greater than 1.5 micrometers and the at least one of a correlation between the geographic area and the plurality of locations or a correlation between the meteorological data and the plurality of locations;

determining a road dust signature based on the portion of the particulate matter data having the size range greater than 1.5 micrometers and a correlation with mobile platform speed; and determining a construction dust signature based on the portion of the particulate matter data having a size range greater than 1.5 micrometers and a correlation between the geographic area and the portion of particulate matter greater than 1.5 micrometers; and wherein the source identifying further includes identifying at least one of sea spray source based on the sea salt signature, a road dust source based on the road dust signature, and a construction source based on the construction dust signature.

6. A system, comprising:

a processor configured to:

receive sensor data, the sensor data including measurements of a plurality of environmental components at a plurality of locations, the measurements made using a plurality of mobile sensor platforms, the environmental components including particulate matter having a size range and a plurality of ambient gases, the sensor data including particulate matter data having the size range and ambient gas data captured at the plurality of locations, wherein the ambient gas data includes nitrogen dioxide data, wherein the particulate matter data includes black carbon data;

determine a signature based on the particulate matter data including the size range and at least one additional factor, the at least one additional factor including the ambient gas data, wherein the at least one additional factor further includes a temporal factor indicating a wildfire, wherein the signature is a diesel combustion signature, and wherein the determining of the signature includes to:

determine the diesel combustion signature based on the nitrogen dioxide data indicating an ambient gas enhancement in nitrogen dioxide and the black carbon data indicating an enhancement in black carbon, wherein the temporal factor indicates a presence of the wildfire; and in response to a determination that the temporal factor indicates the presence of the wildfire, determine a wildfire signature;

identify a source based on the signature, comprising to:

identify at least one diesel combustion source based on the diesel combustion signature; and perform a mitigation measure based on pollutants output by the identified source; and a memory coupled with the processor and configured to provide the processor with instructions.

7. The system of claim 6, wherein a portion of the particulate matter has a size range of less than 0.5 micrometer, and wherein to determine the signature, the processor is further configured to:

determine the diesel combustion signature based a first enhancement of a first ratio of nitrogen dioxide to carbon dioxide, a second enhancement in a second ration of black carbon to carbon dioxide, and a third enhancement in a third ratio of the portion of the data to carbon dioxide.

8. The system of claim 6, wherein the source is an area of spatial impact, the diesel combustion signature indicating the area of spatial impact has higher or lower diesel emissions than another region.

9. The system of claim 6, wherein the signature is a non-diesel combustion signature, wherein the plurality of ambient gases includes carbon monoxide, carbon dioxide, and volatile organic compounds (VOC), wherein the ambient gas data includes carbon monoxide data, carbon dioxide data, and VOC data, and wherein to determine the signature the processor is further configured to:

determine the non-diesel combustion signature based on the carbon dioxide data and the carbon monoxide data indicating an enhancement in a ratio of the carbon monoxide to the carbon dioxide, the VOC data indicating a VOC enhancement, and a lack of a particulate matter enhancement corresponding to black carbon; and wherein to identify the source the processor is further configured to identify at least one non-diesel combustion source based on the diesel combustion signature.

10. The system of claim 6, wherein the at least one additional factor includes at least one of a geographic area, mobile platform speed, or meteorological data, and wherein to determine the signature the processor is further configured to at least one of:

determine a sea salt signature based on a portion of the particulate matter data having a size range of greater than 1.5 micrometers and the at least one of a correlation between the geographic area and the plurality of locations or a correlation between the meteorological data and the plurality of locations;

determine a road dust signature based on the portion of the particulate matter data having the size range greater than 1.5 micrometers and mobile platform speed; and determine a construction dust signature based on the portion of the particulate matter data having a size range greater than 1.5 micrometers and a correlation between the geographic area and the portion of particulate matter greater than 1.5 micrometers; and wherein to identify the source, the processor is further configured to identify at least one of a sea spray source based on the sea salt signature, a road dust source based on the road dust signature, and a construction source based on the construction dust signature.

11. A computer program product embodied in a non-transitory computer readable medium and comprising computer instructions for:

measuring a plurality of environmental components at a plurality of locations using a plurality of mobile sensor platforms to provide sensor data, the environmental components including particulate matter having a size range and a plurality of ambient gases, the sensor data including particulate matter data having the size range and ambient gas data captured at the plurality of locations, wherein the ambient gas data includes nitrogen dioxide data, wherein the particulate matter data includes black carbon data;

determining a signature based on the particulate matter data including the size range and at least one additional factor, the at least one additional factor including the ambient gas data, wherein the at least one additional factor further includes a temporal factor indicating a wildfire, wherein the signature is a diesel combustion signature, and wherein the determining of the signature includes:

determining the diesel combustion signature based on the nitrogen dioxide data indicating an ambient gas enhancement in nitrogen dioxide and the black carbon data indicating an enhancement in black carbon, wherein the temporal factor indicates a presence of the wildfire; and in response to a determination that the temporal factor indicates the presence of the wildfire, determining a wildfire signature;

identifying a source based on the signature, comprising:
identifying at least one diesel combustion source based on the diesel combustion signature; and performing a mitigation measure based on pollutants output by the identified source.

12. The computer program product of claim 11, wherein a portion of the particulate matter has a size range of less than 0.5 micrometer, and wherein the instructions for determining the signature further include computer instructions for:

determining the diesel combustion signature based on a first enhancement in a first ratio of nitrogen dioxide to carbon dioxide, a second enhancement in a second ratio of black carbon to carbon dioxide, and a third enhancement in a third ratio of the portion of the particulate matter data to carbon dioxide.

13. The computer program product of claim 11, wherein the signature is a non-diesel combustion signature, wherein the plurality of ambient gases includes carbon monoxide, carbon dioxide, and volatile organic compounds (VOC), wherein the ambient gas data includes carbon monoxide data, carbon dioxide data, and VOC data, and wherein the computer instructions for determining the signature further include computer instructions for:

determining the non-diesel combustion signature based on the carbon dioxide data and the carbon monoxide data indicating an enhancement in a ratio of the carbon monoxide to the carbon dioxide, the VOC data indicating a VOC enhancement, and a lack of a particulate matter enhancement corresponding to black carbon a lack of a particulate matter enhancement corresponding to a portion of the size range less than 0.5 micrometer; and wherein the identifying further includes identifying at least one non-diesel combustion source based on the diesel combustion signature.

* * * * *